United States Patent
Syed et al.

(10) Patent No.: US 10,857,014 B2
(45) Date of Patent: Dec. 8, 2020

(54) MODIFIED FIXED FLAT WIRE BIFURCATED CATHETER AND ITS APPLICATION IN LOWER EXTREMITY INTERVENTIONS

(71) Applicant: RAM MEDICAL INNOVATIONS, LLC, Springfield, OH (US)

(72) Inventors: Mubin I. Syed, Springfield, OH (US); Azim Shaikh, Beavercreek, OH (US); Suresh Pai, Los Altos, CA (US); Celso Bagaoisan, Union City, CA (US)

(73) Assignee: RAM MEDICAL INNOVATIONS, LLC, Springfield, OH (US)

( * ) Notice: Subject to any disclaimer, the term of this patent is extended or adjusted under 35 U.S.C. 154(b) by 122 days.

(21) Appl. No.: 16/183,066

(22) Filed: Nov. 7, 2018

(65) Prior Publication Data
US 2019/0255286 A1  Aug. 22, 2019

Related U.S. Application Data

(60) Provisional application No. 62/631,904, filed on Feb. 18, 2018.

(51) Int. Cl.
  *A61F 2/954* (2013.01)
  *A61F 2/966* (2013.01)
  (Continued)

(52) U.S. Cl.
  CPC ........ *A61F 2/954* (2013.01); *A61B 17/32056* (2013.01); *A61F 2/966* (2013.01);
  (Continued)

(58) Field of Classification Search
  CPC .......... A61B 17/12109; A61B 17/1214; A61B 17/3468; A61B 2017/1205;
  (Continued)

(56) References Cited

U.S. PATENT DOCUMENTS 3,896,815 A * 7/1975 Fettel ............... A61B 17/22032
                                                   606/194
4,243,040 A    1/1981 Beecher
(Continued)

FOREIGN PATENT DOCUMENTS

| CN | 108472124 | 8/2018 |
| CN | 108472472 | 8/2018 |

(Continued)

OTHER PUBLICATIONS

International Search Report and Written Opinion for International Application No. PCT/US2013/071271 dated Feb. 10, 2014, 7 pages.
(Continued)

*Primary Examiner* — Jocelin C Tanner
(74) *Attorney, Agent, or Firm* — Jennifer Hayes; Nixon Peabody LLP

(57) ABSTRACT

A bifurcated catheter and methods of use are disclosed herein. The bifurcated catheter can include a fixed flat wire that is configurable as a stabilization wire. The bifurcated catheter can be configured to improve the initial access and directability by application of a pull force to the stabilization wire, in addition to a push force from the proximal end of the bifurcated catheter. The stabilization wire is anchored once the bifurcated catheter is positioned. The anchored, bifurcated catheter provides stability and pushability to assist the procedural catheter in traversing the tortuous peripheral vasculature.

16 Claims, 9 Drawing Sheets

(51) Int. Cl.
*A61M 25/01* (2006.01)
*A61B 17/3205* (2006.01)
*A61M 25/06* (2006.01)
*A61B 17/00* (2006.01)
*A61B 17/221* (2006.01)

(52) U.S. Cl.
CPC .... *A61M 25/0102* (2013.01); *A61M 25/0108* (2013.01); *A61B 2017/00358* (2013.01); *A61B 2017/2212* (2013.01); *A61M 2025/0177* (2013.01); *A61M 2025/0681* (2013.01)

(58) Field of Classification Search
CPC ........... A61B 2017/22095; A61F 2/954; A61F 2/966; A61F 2002/9583; A61M 25/003; A61M 25/0082; A61M 25/0102; A61M 25/0108; A61M 25/01; A61M 25/0662; A61M 2025/0096; A61M 2025/0177; A61M 2025/0681
See application file for complete search history.

(56) References Cited

U.S. PATENT DOCUMENTS

| | | | |
|---|---|---|---|
| 4,790,331 A | 12/1988 | Okada et al. | |
| 5,098,707 A | 3/1992 | Baldwin et al. | |
| 5,293,772 A | 3/1994 | Carr, Jr. | |
| 5,344,426 A | 9/1994 | Lau et al. | |
| 5,419,777 A | 5/1995 | Hofling | |
| 5,433,705 A | 7/1995 | Giebel et al. | |
| 5,571,135 A | 11/1996 | Fraser et al. | |
| 5,651,366 A | 7/1997 | Liang et al. | |
| 5,662,703 A | 9/1997 | Yurek et al. | |
| 5,669,924 A | 9/1997 | Shaknovich | |
| 5,690,644 A | 11/1997 | Yurek et al. | |
| 5,718,702 A | 2/1998 | Edwards | |
| 5,720,735 A | 2/1998 | Dorros | |
| 5,766,192 A | 6/1998 | Zacca | |
| 5,807,330 A | 9/1998 | Teitelbaum | |
| 5,813,976 A | 9/1998 | Filipi et al. | |
| 5,824,055 A | 10/1998 | Spiridigliozzi | |
| 5,957,901 A | 9/1999 | Mottola et al. | |
| 5,997,563 A | 12/1999 | Kretzers | |
| 6,027,462 A | 2/2000 | Greene et al. | |
| 6,059,813 A | 5/2000 | Vrba et al. | |
| 6,070,589 A | 6/2000 | Keith et al. | |
| 6,152,141 A | 11/2000 | Stevens et al. | |
| 6,238,410 B1 | 5/2001 | Vrba et al. | |
| 6,245,017 B1 | 6/2001 | Hashimoto | |
| 6,245,573 B1 | 6/2001 | Spillert | |
| 6,428,567 B2 | 8/2002 | Wilson et al. | |
| 6,450,964 B1 | 9/2002 | Webler | |
| 6,464,665 B1 | 10/2002 | Heuser | |
| 6,494,875 B1 | 12/2002 | Mauch | |
| 6,544,278 B1 | 4/2003 | Vrba et al. | |
| 6,663,613 B1 | 12/2003 | Lewis et al. | |
| 6,764,505 B1 | 7/2004 | Hossainy et al. | |
| 6,780,174 B2 | 8/2004 | Mauch | |
| 6,808,520 B1 | 10/2004 | Fouirkas et al. | |
| 6,837,881 B1 | 1/2005 | Barbut | |
| 6,929,633 B2 | 8/2005 | Evans et al. | |
| 6,932,829 B2 | 8/2005 | Majercak | |
| 6,942,682 B2 | 9/2005 | Vrba et al. | |
| 7,235,083 B1 | 6/2007 | Perez et al. | |
| 7,393,358 B2 | 7/2008 | Malewicz | |
| 7,651,520 B2 | 1/2010 | Fischell et al. | |
| 7,674,493 B2 | 3/2010 | Hossainy et al. | |
| 7,740,791 B2 | 6/2010 | Kleine et al. | |
| 7,758,624 B2 | 7/2010 | Dorn et al. | |
| 7,763,010 B2 | 7/2010 | Evans et al. | |
| 7,766,961 B2 | 8/2010 | Patel et al. | |
| 7,828,832 B2 | 11/2010 | Belluche et al. | |
| 7,842,026 B2 | 11/2010 | Cahill et al. | |
| 7,955,370 B2 | 6/2011 | Gunderson | |
| 8,092,509 B2 | 1/2012 | Dorn et al. | |
| 8,119,184 B2 | 2/2012 | Hossainy et al. | |
| 8,202,309 B2 | 6/2012 | Styrc | |
| 8,241,241 B2 | 8/2012 | Evans et al. | |
| 8,343,181 B2 | 1/2013 | Duffy et al. | |
| 8,419,767 B2 | 4/2013 | Al-Qbandi et al. | |
| 8,535,290 B2 | 9/2013 | Evans et al. | |
| 8,721,714 B2 | 5/2014 | Kelley | |
| 8,727,988 B2 | 5/2014 | Flaherty et al. | |
| 8,728,144 B2 | 5/2014 | Fearnot | |
| 8,740,971 B2 | 6/2014 | Iannelli | |
| 8,986,241 B2 | 3/2015 | Evans et al. | |
| 8,998,894 B2 | 4/2015 | Mauch et al. | |
| 9,301,830 B2 | 4/2016 | Heuser et al. | |
| 9,314,499 B2 | 4/2016 | Wang et al. | |
| 9,636,244 B2 | 5/2017 | Syed | |
| 9,855,705 B2 | 1/2018 | Wang et al. | |
| 9,980,838 B2 | 5/2018 | Syed | |
| 2001/0003985 A1 | 6/2001 | Lafontaine et al. | |
| 2001/0049534 A1 | 12/2001 | Lachat | |
| 2002/0077691 A1 | 6/2002 | Nachtigall | |
| 2002/0123698 A1 | 9/2002 | Garibotto et al. | |
| 2002/0156518 A1 | 10/2002 | Tehrani | |
| 2002/0165535 A1 | 11/2002 | Lesh | |
| 2003/0088187 A1 | 5/2003 | Saadat et al. | |
| 2003/0204171 A1 | 10/2003 | Kucharczyk | |
| 2003/0216721 A1 | 11/2003 | Diederich | |
| 2003/0229282 A1 | 12/2003 | Burdette | |
| 2004/0002714 A1 | 1/2004 | Weiss | |
| 2004/0073190 A1 | 4/2004 | Deem et al. | |
| 2004/0087995 A1 | 5/2004 | Copa et al. | |
| 2004/0138734 A1 | 7/2004 | Chobotov et al. | |
| 2004/0147837 A1 | 7/2004 | MacAulay et al. | |
| 2004/0167463 A1* | 8/2004 | Zawacki | A61M 25/0026 604/43 |
| 2004/0089249 A1 | 10/2004 | Cook | |
| 2005/0043779 A1 | 2/2005 | Wilson | |
| 2005/0085841 A1 | 4/2005 | Eversull et al. | |
| 2005/0101968 A1 | 5/2005 | Dadourian | |
| 2005/0113798 A1 | 5/2005 | Slater | |
| 2005/0113862 A1 | 5/2005 | Besselink et al. | |
| 2005/0222488 A1 | 10/2005 | Chang et al. | |
| 2005/0234499 A1 | 10/2005 | Olson et al. | |
| 2005/0251160 A1 | 11/2005 | Saadat et al. | |
| 2005/0267010 A1* | 12/2005 | Goodson | A61P 11/00 514/12.4 |
| 2006/0025752 A1 | 2/2006 | Broaddus et al. | |
| 2006/0025844 A1 | 2/2006 | Majercak et al. | |
| 2006/0030923 A1 | 2/2006 | Gunderson | |
| 2006/0036218 A1 | 2/2006 | Goodson et al. | |
| 2006/0155363 A1 | 7/2006 | Laduca et al. | |
| 2006/0200221 A1 | 9/2006 | Malewicz | |
| 2006/0257389 A1 | 11/2006 | Binford | |
| 2006/0259063 A1 | 11/2006 | Bates et al. | |
| 2006/0270900 A1 | 11/2006 | Chin et al. | |
| 2007/0016019 A1 | 1/2007 | Salgo | |
| 2007/0016062 A1 | 1/2007 | Park | |
| 2007/0038061 A1 | 2/2007 | Huennekens et al. | |
| 2007/0038293 A1 | 2/2007 | St. Goar et al. | |
| 2007/0049867 A1 | 3/2007 | Shindelman | |
| 2007/0083215 A1 | 4/2007 | Hamer et al. | |
| 2007/0118151 A1 | 5/2007 | Davidson et al. | |
| 2007/0129719 A1 | 6/2007 | Kendale et al. | |
| 2007/0219614 A1 | 9/2007 | Hartley et al. | |
| 2007/0288082 A1 | 12/2007 | Williams | |
| 2008/0039746 A1 | 2/2008 | Hissong et al. | |
| 2008/0114239 A1 | 5/2008 | Randall et al. | |
| 2008/0194993 A1 | 8/2008 | McLaren et al. | |
| 2008/0208309 A1 | 8/2008 | Saeed | |
| 2008/0281398 A1 | 11/2008 | Koss | |
| 2008/0306467 A1* | 12/2008 | Reydel | A61M 25/0068 604/523 |
| 2009/0005679 A1 | 1/2009 | Dala-Krishna | |
| 2009/0018526 A1 | 1/2009 | Power et al. | |
| 2009/0036780 A1 | 2/2009 | Abraham | |
| 2009/0093791 A1 | 4/2009 | Heuser | |
| 2009/0132019 A1 | 5/2009 | Duffy et al. | |
| 2009/0171293 A1 | 7/2009 | Yang et al. | |
| 2009/0177035 A1 | 7/2009 | Chin | |
| 2009/0240253 A1 | 9/2009 | Murray | |

(56) References Cited

U.S. PATENT DOCUMENTS

| | | |
|---|---|---|
| 2009/0254116 A1 | 10/2009 | Rosenschein et al. |
| 2009/0270975 A1 | 10/2009 | Gifford, III et al. |
| 2009/0319017 A1 | 12/2009 | Berez et al. |
| 2010/0016943 A1 | 1/2010 | Chobotov |
| 2010/0024818 A1 | 2/2010 | Stenzler et al. |
| 2010/0030165 A1 | 2/2010 | Takagi et al. |
| 2010/0030256 A1 | 2/2010 | Dubrul et al. |
| 2010/0069852 A1 | 3/2010 | Kelley |
| 2010/0168583 A1 | 7/2010 | Dausch et al. |
| 2010/0185161 A1 | 7/2010 | Pellegrino et al. |
| 2010/0185231 A1 | 7/2010 | Lashinski |
| 2010/0204708 A1 | 8/2010 | Sharma |
| 2010/0211095 A1 | 8/2010 | Carpenter |
| 2010/0268067 A1 | 10/2010 | Razzaque et al. |
| 2010/0272740 A1 | 10/2010 | Vertegel et al. |
| 2010/0298922 A1 | 11/2010 | Thornton et al. |
| 2011/0009943 A1 | 1/2011 | Paul et al. |
| 2011/0034987 A1 | 2/2011 | Kennedy |
| 2011/0071394 A1 | 3/2011 | Fedinec |
| 2011/0082533 A1 | 4/2011 | Vardi et al. |
| 2011/0213459 A1 | 9/2011 | Garrison |
| 2011/0224773 A1 | 9/2011 | Gifford et al. |
| 2011/0230830 A1 | 9/2011 | Gifford, III et al. |
| 2011/0270375 A1 | 11/2011 | Hartley et al. |
| 2012/0016343 A1 | 1/2012 | Gill |
| 2012/0020942 A1 | 1/2012 | Hall et al. |
| 2012/0022636 A1 | 1/2012 | Chobotov |
| 2012/0029478 A1 | 2/2012 | Kurosawa |
| 2012/0034205 A1 | 2/2012 | Alkon |
| 2012/0035590 A1 | 2/2012 | Whiting et al. |
| 2012/0169712 A1 | 7/2012 | Hill et al. |
| 2012/0209375 A1 | 8/2012 | Madrid et al. |
| 2012/0221094 A1 | 8/2012 | Cunningham |
| 2012/0289945 A1 | 11/2012 | Segermark |
| 2013/0053792 A1 | 2/2013 | Fischell et al. |
| 2013/0131777 A1 | 5/2013 | Hartley et al. |
| 2013/0296773 A1 | 11/2013 | Feng et al. |
| 2013/0310823 A1 | 11/2013 | Gelfand et al. |
| 2013/0331819 A1 | 12/2013 | Rosenman et al. |
| 2013/0331921 A1 | 12/2013 | Roubin |
| 2014/0031925 A1 | 1/2014 | Garrison et al. |
| 2014/0142427 A1 | 5/2014 | Petroff |
| 2014/0214002 A1 | 7/2014 | Thermopeutix |
| 2014/0228808 A1 | 8/2014 | Webster et al. |
| 2014/0276602 A1 | 9/2014 | Bonnette |
| 2014/0358123 A1 | 12/2014 | Ueda et al. |
| 2015/0018942 A1 | 1/2015 | Hung et al. |
| 2015/0174377 A1 | 6/2015 | Syed |
| 2015/0190576 A1 | 7/2015 | Lee et al. |
| 2015/0201900 A1 | 7/2015 | Syed |
| 2015/0245933 A1 | 9/2015 | Syed |
| 2015/0250991 A1 | 9/2015 | Silvestro |
| 2015/0352331 A1 | 12/2015 | Helm, Jr. |
| 2015/0366536 A1 | 12/2015 | Courtney et al. |
| 2015/0374261 A1 | 12/2015 | Grunwald |
| 2016/0008058 A1 | 1/2016 | Hu et al. |
| 2016/0038724 A1 | 2/2016 | Madsen et al. |
| 2016/0120509 A1 | 5/2016 | Syed |
| 2016/0120673 A1 | 5/2016 | Siegel et al. |
| 2016/0296355 A1 | 10/2016 | Syed |
| 2016/0338835 A1 | 11/2016 | Bioventrix |
| 2017/0119562 A1 | 5/2017 | Syed |
| 2017/0119563 A1 | 5/2017 | Syed |
| 2017/0135833 A1 | 5/2017 | Syed |
| 2017/0181876 A1 | 6/2017 | Syed |
| 2017/0304095 A1 | 10/2017 | Syed |
| 2017/0361062 A1 | 12/2017 | Syed |
| 2018/0042743 A1 | 2/2018 | Syed |
| 2018/0059124 A1 | 3/2018 | Syed |
| 2018/0116780 A1 | 5/2018 | Laine |
| 2018/0250147 A1 | 9/2018 | Syed |
| 2019/0091441 A1 | 3/2019 | Syed |
| 2019/0254675 A1 | 8/2019 | Syed |
| 2019/0336114 A1 | 11/2019 | Syed |
| 2020/0038210 A1 | 2/2020 | Syed |

FOREIGN PATENT DOCUMENTS

| | | |
|---|---|---|
| CN | 108882975 A | 11/2018 |
| CN | 109475722 A | 3/2019 |
| CN | 111629696 A1 | 9/2020 |
| EP | 3280355 | 2/2018 |
| EP | 3367969 | 9/2018 |
| EP | 3368123 | 9/2018 |
| EP | 3399944 A1 | 11/2018 |
| EP | 3405261 A1 | 11/2018 |
| EP | 3471815 A1 | 4/2019 |
| IN | 201827018555 | 10/2018 |
| IN | 201827018768 | 10/2018 |
| WO | WO 1996/036269 | 11/1996 |
| WO | 2004089249 A1 | 10/2004 |
| WO | WO 2010/129193 | 11/2010 |
| WO | WO 2011/011539 | 1/2011 |
| WO | WO 2011/106502 | 9/2011 |
| WO | WO 2011/137336 | 11/2011 |
| WO | WO 2012/030101 | 8/2012 |
| WO | WO 2014/081947 | 5/2014 |
| WO | WO 2014/197839 | 12/2014 |
| WO | WO 2016164215 | 10/2016 |
| WO | WO 2017/074492 | 5/2017 |
| WO | WO 2017/074536 | 5/2017 |
| WO | WO 2017/127127 | 7/2017 |
| WO | WO 2017/222571 | 12/2017 |
| WO | WO 2017/222612 | 12/2017 |
| WO | WO 2018/164766 | 9/2018 |
| WO | 2019/070349 A1 | 4/2019 |
| WO | 2019/160625 A1 | 8/2019 |
| WO | 2019/160626 A1 | 8/2019 |

OTHER PUBLICATIONS

International Preliminary Report on Patentability issued in International Application No. PCT/US2013/071271 dated May 26, 2015, 6 pages.

International Search Report and Written Opinion issued for International Application No. PCT/US2016/024794 dated Jul. 1, 2016, 10 pages.

International Search Report and Written Opinion for International Application No. PCT/US2016/024795 dated Aug. 30, 2016, 14 pages.

International Search Report and Written Opinion issued for International Application No. PCT/US2016/047163 dated Oct. 28, 2016, 9 pages.

International Search Report and Written Opinion issued for International Application No. PCT/US2016/047165 dated Jan. 5, 2017, 13 pages.

International Search Report and Written Opinion issued for International Application No. PCT/US2017/021188 dated May 10, 2017, 11 pages.

International Search Report and Written Opinion issued for International Application No. PCT/US2018/012834 dated Mar. 15, 2018, 13 pages.

International Preliminary Report on Patentability issued in International Application No. PCT/US2016/024795 dated May 1, 2018, 10 pages.

International Preliminary Report on Patentability issued in International Application No. PCT/US2016/047165 dated May 1, 2018, 5 pages.

Beckman et al., Venous Thromboembolism: A Public Health Concern, Am J Prev Med., 2010, vol. 38(4), pp. S495-S501.

Godwin, J., The Circulatory and Respiratory Systems, Z0250 Lab III, 2002, retrieved from: https://projects.ncsu.edu/cals/course/zo250/lab-3.html.

Meunier et al., Individual Lytic Efficacy of Recombinant Tissue Plasminogen Activator in an in-vitro Human Clot Model: Rate of Nonresponse Acad Emerg Med., 2013, vol. 20(5), pp. 449-455.

Schwartz et al., Intracardiac Echocardiography in Humans using a Small-Sized (6F), Low Frequency (12.5 MHz) Ultrasound Catheter Methods, Imaging Planes and Clinical Experience, Journal of the American College of Cardiology, 1993, vol. 21(1), pp. 189-198.

(56) References Cited

OTHER PUBLICATIONS

Tripathi et al., Use of Tissue Plasminogen Activator for Rapoid Dissolution of Fibrin and Blood Clots in the Eye After Surgery for Claucomoa and Cataract in Humans, Drug Development Research, 1992, vol. 27(2), pp. 147-159.
Stroke Treatments, American Heart Association, Retrieved from: http://www.strokeassociation.org/STROKEORG/AboutStroke/Treatment/Stroke-Treatments_UCM_310892_Article.jsp#V9Hrg2WfV_1 on Sep. 8, 2016.
Blaney et al., Alteplase for the Treatment of Central Venous Catheter Occlusion in Children: Results of a Prospective, Open-Label, Single-Arm Study (The Cathflo Activase Pediatric Study).
Shah, T., Radiopaque Polymer Formulations for Medical Devices, MDDI Medical Diagnostic and Device Industry: Materials, 2001, retrieved from: https://www.mddionline.com/radiopaque-polymer-formulations-medical-devices.
International Preliminary Report on Patentability issued for PCT/US2016/047163 dated Dec. 25, 2018, 7 pages.
International Preliminary Report on Patentability issued for PCT/US2017/021188 dated Dec. 25, 2018, 9 pages.
International Search Report and Written Opinion for PCT/US2018/047372 dated Jan. 2, 2019, 8 pages.
International Search Report and Written Opinion for PCT/US2019/012727 dated Mar. 21, 2019, 12 pages.
International Search Report and Written Opinion for PCT/US2019/12745 dated Apr. 1, 2019, 10 pages.
EP 16777055.1 Extended Search Report dated Feb. 12, 2019, 7 pages.
EP 18725097.2 Extended Search Report dated Apr. 24, 2019, 9 pages.
EP 16860437.9 Extended Search Report dated May 17, 2019.
EP 16860409.8 Extended Search Report dated Jun. 27, 2019.
EP 16906475.5 Extended Search Report dated Jan. 24, 2020.
EP 17815838.2 Extended Search Report dated Jan. 20, 2020.

\* cited by examiner

US 10,857,014 B2

MODIFIED FIXED FLAT WIRE BIFURCATED CATHETER AND ITS APPLICATION IN LOWER EXTREMITY INTERVENTIONS

CROSS REFERENCE TO RELATED APPLICATIONS

This application claims priority under 35 U.S.C. § 119 to U.S. Provisional Application No. 62/631,904, entitled "MODIFIED FIXED FLAT WIRE BIFURCATED CATHETER AND ITS APPLICATION IN AORTO BIFEMORAL BYPASS," and filed on Feb. 18, 2018. The contents of that application are hereby incorporated by reference in their entirety.

TECHNICAL FIELD

The present disclosure relates to improved methods and apparatuses for traversing a tortuous vasculature. Specifically, the present disclosure relates to providing support to procedural catheters during lower extremity intervention procedures to traverse the procedural site through the tortuous access vessels.

BACKGROUND

Technology associated with interventional procedures is ever developing, particularly in the areas of stenting and balloon angioplasty of Interventional procedures are typically challenging, as accessing various regions of the artery can be dependent on the anatomical disposition of the access location. Specifically, accessing regions of a tortuous peripheral arteries and performing interventional procedures in a hostile anatomy can be very difficult. Furthermore, the subsequent removal of blockages and placement of a stent delivery system into aorto femoral arteries becomes more difficult, or in some instances impossible. The interventional procedure may also be difficult for the popliteal and tibial arteries. The stenting procedure is meant to re-establish a more normalized blood flow through these tortuous arteries by opening up regions constricted by plaque or embolic deposits, which inhibit blood flow.

Although the stent delivery systems are designed to accommodate very acute bends, they are reliant upon guide catheters, guide wires and/or embolic protection devices during deployment. When long delivery systems in tortuous arteries the pushability of catheters and guide wires become critical. As a result, the rigid or stiff catheters and guide wires are needed to manipulate the tortuous entry. With these type of rigid devices, injuries to the tortuous arteries and access vessels often occur during the insertion, manipulation and stabilization of the stent delivery mechanism. Injuries to the tortuous arteries and access vessels often occur during removal of the guide wires, secondary equipment and wires as well. Specifically, the injuries can be caused by puncturing or cutting into the arterial walls resulting in dissections and trauma to the vessels involved. These traumas can be dangerous to the patient as they can ultimately affect blood flow by leakage at the dissections. In some instances, the traumas can create accumulation of thrombus. Dissections and the accumulation of thrombus can require additional procedures to repair and heal the damaged artery walls.

In view of the foregoing, there exists a need to provide a simplified procedure that reduces the injuries caused to the arterial walls during lower extremity interventions. Furthermore, there exists a need for a usable sheath and catheter stabilization system that enable the use of softer catheters and less stiff guide wires for the treatment of lower extremities.

BRIEF DESCRIPTION OF THE DRAWINGS

In order to describe the manner in which the above-recited disclosure and its advantages and features can be obtained, a more particular description of the principles described above will be rendered by reference to specific examples illustrated in the appended drawings. These drawings depict only example aspects of the disclosure, and are therefore not to be considered as limiting of its scope. These principles are described and explained with additional specificity and detail through the use of the following drawings.

DETAILED DESCRIPTION OF ILLUSTRATED EMBODIMENTS

Figure 1:
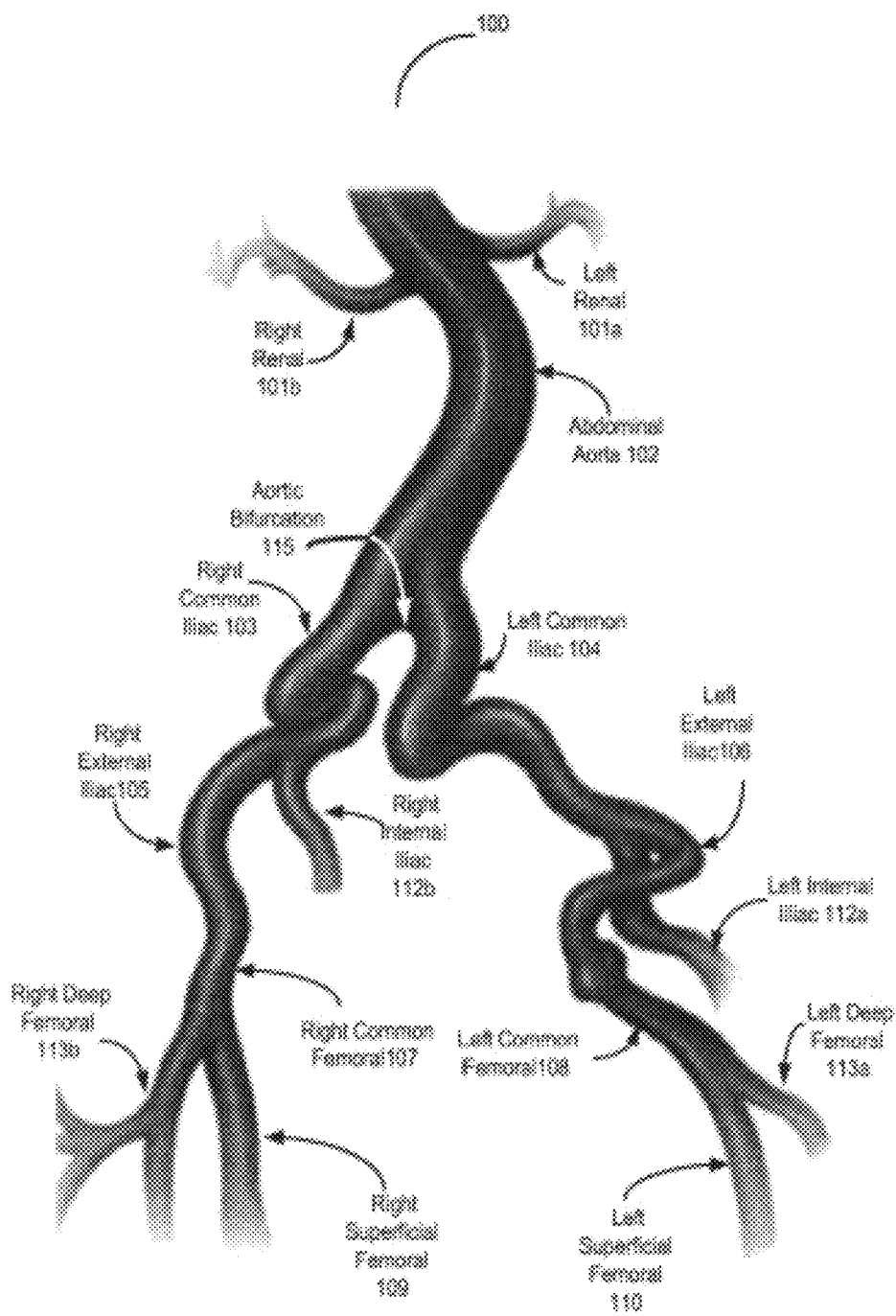
FIG. 1 illustrates tortuous arteries of the lower extremities, in accordance with one embodiment of the disclosure.

The present disclosure is described with reference to the attached figures, where like reference numerals are used throughout the figures to designate similar or equivalent elements. The figures are not drawn to scale, and they are provided merely to illustrate the instant disclosure. Several aspects of the disclosure are described below with reference to example applications for illustration. It should be understood that numerous specific details, relationships, and methods are set forth to provide a full understanding of the disclosure. One having ordinary skill in the relevant art, however, will readily recognize that the disclosure can be practiced without one or more of the specific details, or with other methods. In other instances, well-known structures or operations are not shown in detail to avoid obscuring the disclosure. The present disclosure is not limited by the illustrated ordering of acts or events, as some acts may occur in different orders and/or concurrently with other acts or events. Furthermore, not all illustrated acts or events are required to implement a methodology in accordance with the present disclosure.

The present disclosure provides a system and method for providing access to tortuous arteries to perform lower extremity interventions. The present disclosure is directed towards employing a flat fixed wire bifurcated catheter. The flat fixed wire bifurcated catheter can include a flat wire fixed along the length of the bifurcated catheter from its proximal end to the bifurcation. The flat wire can convert to a normal round stabilization wire as it emerges from a side hole at the bifurcation end of the bifurcated catheter to extend for an additional length beyond the bifurcation. The distal end of the bifurcated catheter can be configured to have a dual lumen (e.g., a large procedural lumen and a small stabilization lumen) from which the flat wire emerges. Alternatively, the distal end of the bifurcated catheter can be configured to have a procedural lumen and a side hole for the stabilization wire.

A small sheath can be provided to enable percutaneous access for the distal end of the support wire. A push and pull force can be applied to the bifurcated catheter using the stabilization wire to enable the bifurcated catheter to traverse the tortuous vessels. This process allows the bifurcated catheter to be positioned in either the common femoral artery or the proximal superficial femoral artery. Furthermore, the stabilization wire can be locked at the accesses to apply tension and stabilization to the procedural lumen.

It should be understood by one of ordinary skill in the art, that the disclosed apparatus can be implemented in any type of lower extremity peripheral arterial intervention. In addition, the apparatus can also be implemented for intervention within the internal iliac artery vascular distribution (e.g., uterine artery embolization, prostate artery embolization, proximal internal iliac artery embolization prior to endovascular common iliac artery aneurysm repair, etc.). As disclosure herein, the disclosed system and method can reduce injury to the vessels within the arteries, reduce trauma caused during the intervention procedure, and improve the procedural success rate. The disclosed system and method can also improve navigation speed through difficult anatomy and enhance stability.

FIG. 1 illustrates an exemplary tortuous vessel artery 100, in accordance with an embodiment of the disclosure. The tortuous vessel artery 100 can include an abdominal aortic bifurcation with tortuous branch arteries. The tortuous branch arteries can include a right renal artery 101b and a left renal artery 101a extending from an abdominal aorta 102. The abdominal aorta 102 can be parted at an aortic bifurcation 115, and connected to arteries of the lower limbs. The arteries of the lower limbs can include a right common iliac 103 and a left common iliac 104. The left common iliac 104 can be split into a left external iliac 106 and a left internal iliac 112a. The left external iliac 106 can be connected to a left common femoral 108, and further split into a left deep femoral 113a, and a left superficial femoral 110.

The right common iliac 103 can be split into a right external iliac 105 and a right internal iliac 112b. The right external iliac 105 can be connected to a right common femoral 107, which splits into a right deep femoral 113b and a right superficial femoral 109. FIG. 1 illustrates the tortuous nature of the peripheral arteries.

When performing interventions within the tortuous vessel artery 100, it is common to encounter difficulties associated with pushability and torque. As the catheters and wires are guided over a highly angulated aortic bifurcation 115 or through the extremely tortuous common iliac arteries 103 and 104, it can be extremely difficult to apply torque. Furthermore, these arteries can contain calcific plaques or other obstructions which can add anatomic and technical challenges with traversing the tortuous vessel artery 100.

Figure 2:
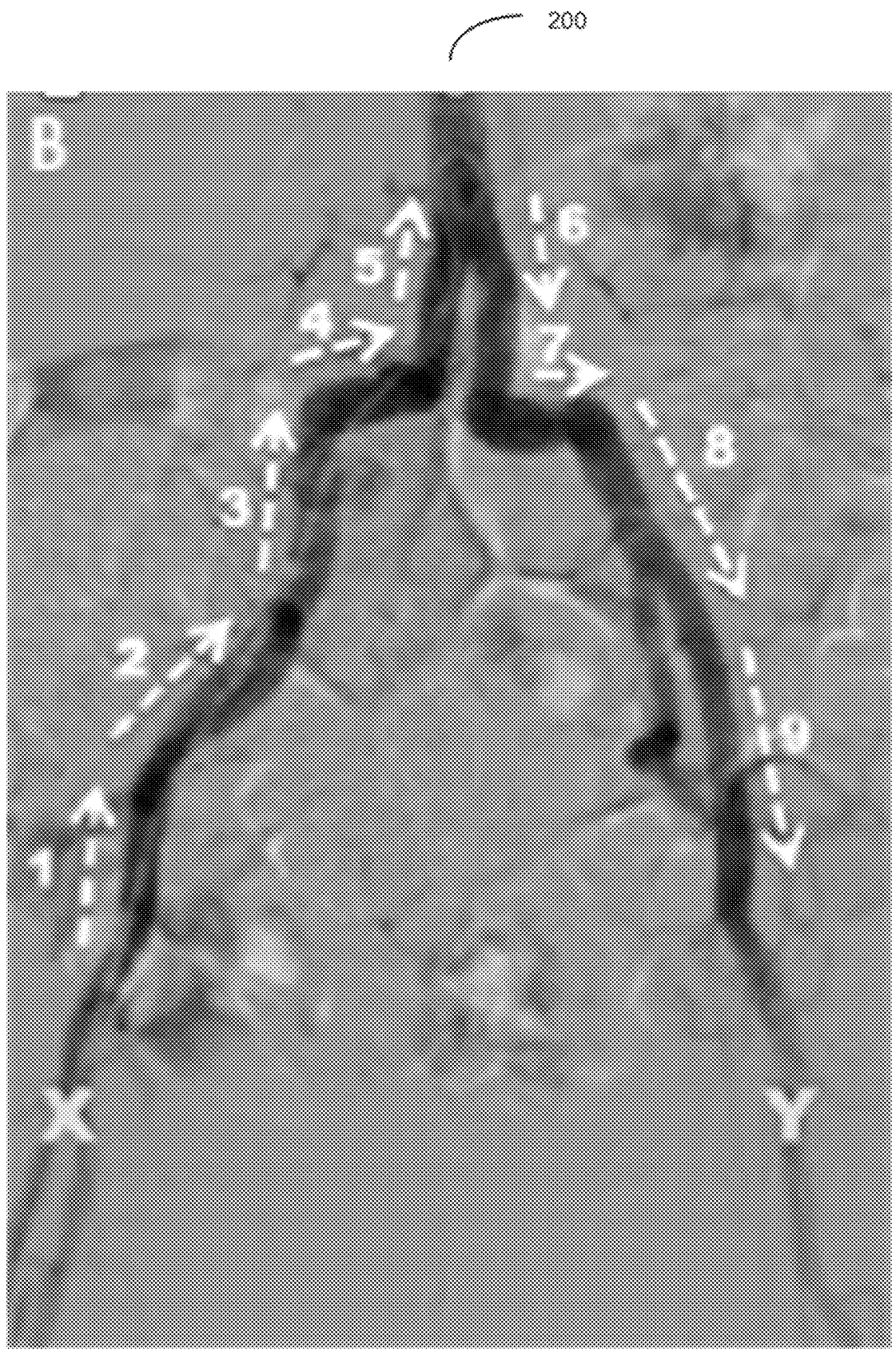
FIG. 2 illustrates the difficulty of access by pushing a sheath from a contralateral percutaneous access at point "X" to the location of a procedure at point Y.

FIG. 2 illustrates a tortuous anatomical pathway 200 from the percutaneous access within the common femoral artery to a potential procedure location on the ipsilateral side, in accordance with an embodiment of the disclosure. In some embodiments, interventional devices such as wires and catheters are pushed from the contralateral access at point 'X' to the treatment site 'Y'. The devices would need to travel through the general pathways 1 through 9. Due to the multi directional twists and turns along the pathways 1 through 9, the devices can suffer from a significant loss of performance such as torque and pushability. While FIG. 2 illustrates the tortuous anatomical pathway 200 in a two-dimensional format, the tortuousity of the anatomical pathway 200 is often significantly more severe, as illustrated in FIG. 1.

Figure 3:
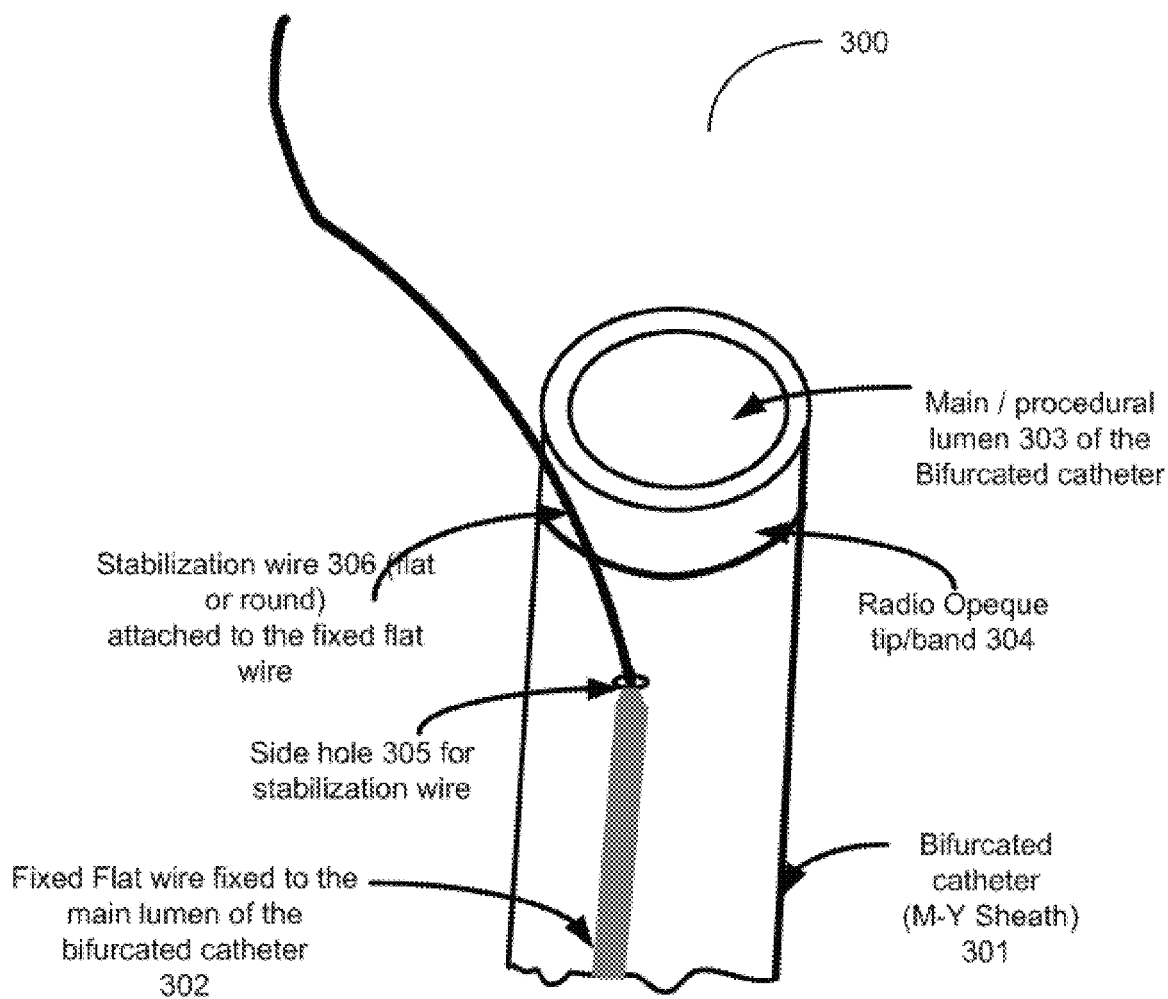
FIG. 3 illustrates the distal end of a fixed flat wire bifurcated catheter in accordance with an embodiment of the disclosure.

FIG. 3 illustrates a bifurcated catheter 300, in accordance with an embodiment of the disclosure. The bifurcated catheter 300 includes a bifurcated sheath 301 and a fixed flat-wire 302. The fixed flat wire 302 can be configured to bifurcate from a bifurcated sheath 301 of the bifurcated catheter 300. The fixed flat wire 302 can bifurcate close to a distal end of the bifurcated catheter 300. In some embodiments, the fixed flat wire 302 can be attached to, or integrated within, the main lumen 303 of the bifurcated catheter 300. This is discussed in greater detail below.

The bifurcated catheter has a proximal end (not shown) and a distal end. In some embodiments, as shown in FIG. 3, the distal end includes a side hole 305 for a stabilization wire 306. The stabilization wire 306 can be an extension of the fixed flat wire 302. Furthermore, the stabilization wire 306 can be attached to or embedded within a wall of the bifurcated sheath 301 of the bifurcated catheter 300. The stabilization wire 306, can extend from the proximal end (not shown) to the side hole 305 at the distal end of the bifurcated catheter 300.

For the purpose of this embodiment, the procedural lumen is illustrated as the main lumen 303 at the distal end of the bifurcated catheter 300. A stabilization wire 306 is also illustrated. In some embodiments, the stabilization wire 306 can be round. In alternative embodiments, the stabilization wire can take on various shapes, including, for example square, oval, hollow, etc., as required for the application of the bifurcated catheter 300. For the purpose of this disclosure, the shape of the stabilization wire 306 exiting from the side hole 305 should not be considered limiting. In some embodiments of the disclosure, the bifurcated catheter 300 includes two lumens (not shown): the procedural lumen 303 and a smaller stabilization lumen (not shown) which has the fixed flat wire 302.

In some embodiments, both lumens span almost the entire length of the bifurcated catheter 300 and bifurcate at the distal end into two independent lumens. In an alternative embodiment, the fixed flat wire 302 can be attached to or embedded into an inner side wall of the stabilization lumen. In some embodiments, the bifurcated catheter 300 bifurcate into two catheters (not shown) close to the distal end of the bifurcated catheter 300. In some embodiments, the two catheters formed at the bifurcation can be configured as a larger, procedural catheter and a smaller, stabilization catheter. In such embodiments, the larger, procedural catheter can include a large lumen, which is a continuation of the procedural lumen 303. The second smaller catheter can include a smaller stabilization lumen configured to carry the stabilization wire.

In some embodiments the bifurcated catheter 300 can include a radio opaque band 304 at its distal end. The radio opaque band 304 can be implemented to track the distal end of the bifurcated catheter 300 as it is advanced through the arteries of FIG. 1. The procedural lumen 303 can extend from its proximal end to its distal end within the bifurcated sheath 301. The stabilization wire 306 can be configured to protrude from the bifurcated catheter 300 at the side hole 305 as an extension of the fixed flat wire 302. In some embodiments, the stabilization wire 306 can extend beyond the end of the bifurcated catheter 300. Typically, such extension can be as much as 6 to 10 cm or more.

As indicated above, the stabilization wire 306 can be a flat wire, a round wire or a wire of any suitable cross-sectional shape. Additionally, the stabilization wire 306 may be sold or hollow. The fixed flat wire 302 and the stabilization wire 306 can be fabricated using commonly known materials in the art including, for example, stainless steel, nickel titanium, composites, metal reinforced polymer, polymer, a combination thereof, or the like.

FIGS. 4 to 8 illustrate an exemplary process for lower extremity intervention implemented using the bifurcated catheter 300 of FIG. 3. While the reference numbers are not always repeated on all the figures to make the figures more readable, the reference numbers are used consistently across all these figures and their descriptions.

The lower extremity intervention can include, for example, an aorto-bifemoral bypass or a tortuous aortoiliac artery treatment. Furthermore, FIGS. 4 to 8 illustrate the process of providing end-to-end stability and improved accessibility to any additional procedural catheter and instruments introduced through the procedural lumen 303 of the bifurcated catheter 300.

Figure 4:
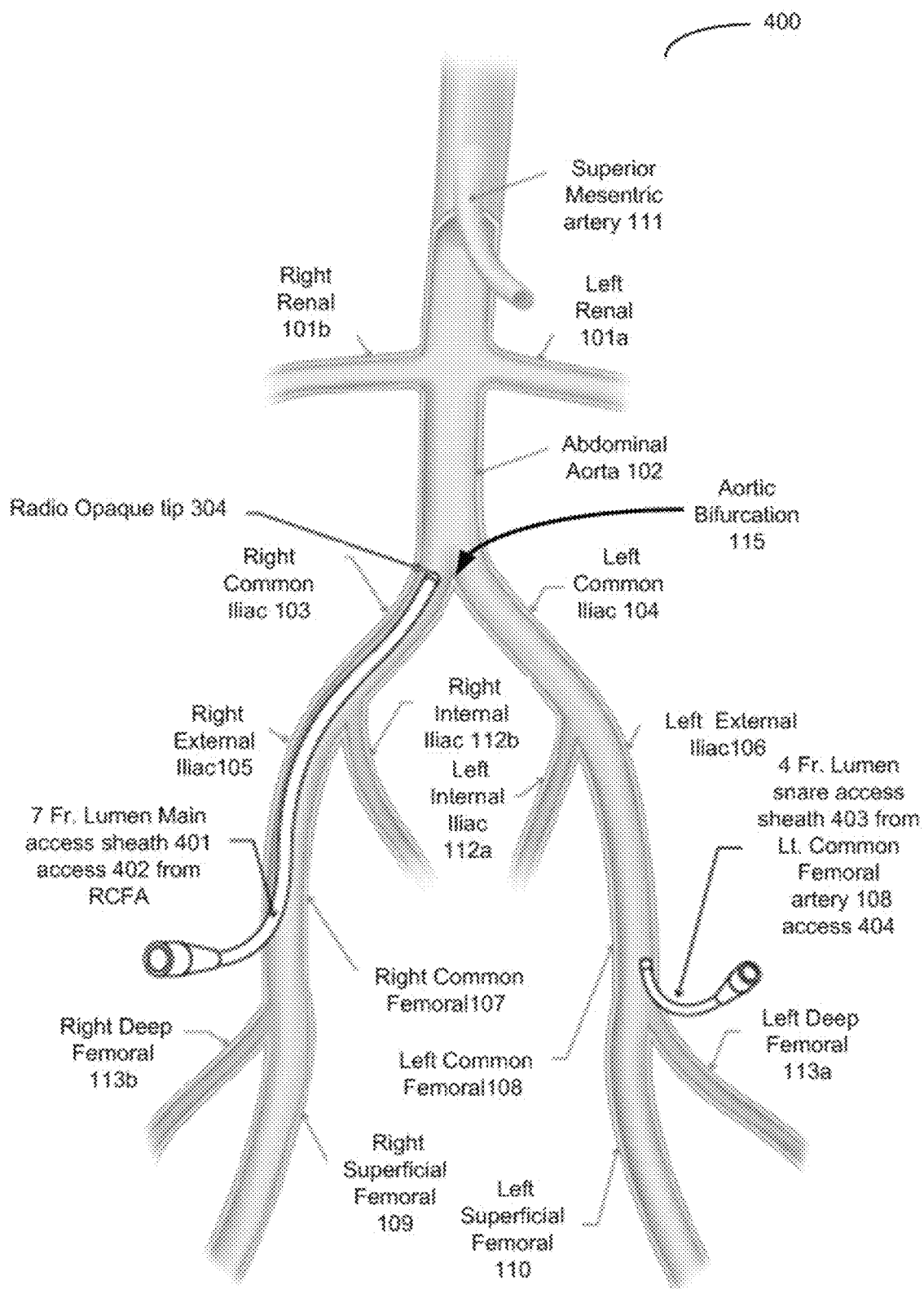
FIG. 4 illustrates the process of establishing a contralateral percutaneous femoral access for the main access sheath and an ipsilateral percutaneous femoral access for the snare access sheath while in accordance with an embodiment of the disclosure.

FIG. 4 illustrates a diagram 400 where a percutaneous contralateral femoral access 402 is introduced into the right common femoral artery 107. The percutaneous contralateral femoral access 402 can be implemented to introduce a main access sheath 401 into the right common femoral artery 107. The main access sheath 401 can be configured as a 7 Fr. vascular sheath. The main access sheath 401 can be advanced through the right external 105 and right common iliac 103 to the aortic bifurcation 115. The main access sheath 401 can be tracked using a radio opaque band 304 as the main access sheath 401 is advanced to the aortic bifurcation 115. FIG. 4 also illustrates the introduction of a percutaneous ipsilateral femoral access 404 into the left common femoral artery 108. The percutaneous ipsilateral femoral access 404 is introduced for a snare access sheath 403 of a 4 Fr. internal lumen.

Figure 5:
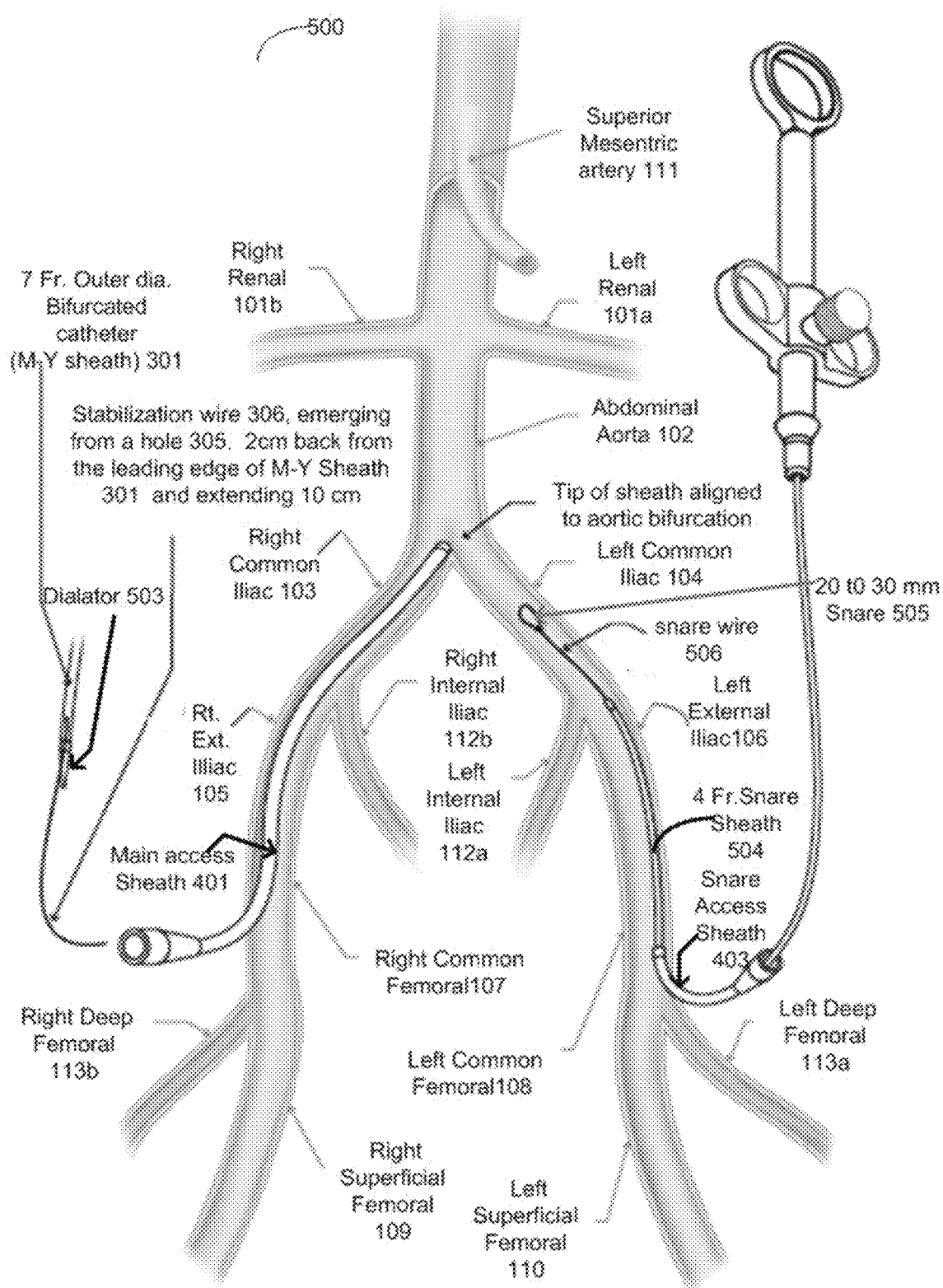
FIG. 5 illustrates the process of inserting a snare catheter and extending a snare wire having a snare at its distal end to the aortic bifurcation through the ipsilateral access, in accordance with an embodiment of the disclosure.

FIG. 5 illustrates a process for introducing a snare catheter and extending a snare wire to an aortic bifurcation, in accordance with an embodiment of the disclosure. Once the main access sheaths 401 and 403 are in place, a 4 Fr snare sheath 504 and snare wire 506 are introduced through the retrograde snare access sheath 403. In some embodiments, the snare wire 506 includes a snare 505 at its distal end extending to the aortic bifurcation 115. The snare 505 can be 20 to 30 mm (or smaller) in diameter. In some embodiments, the fixed flat wire bifurcated catheter 300 includes a dilator 503 in the main sheath. The fixed flat wire bifurcated catheter 300 and the stabilization wire 306 are introduced through the main access sheath 401. The main access sheath 401 includes the distal end, the tip of the main access sheath aligned to the aortic bifurcation 115. FIG. 5 further illustrates the fixed flat wire bifurcated catheter 300 having a bifurcated sheath 301 and the stabilization wire 306 being pushed through the distal end of the main access sheath 401. The stabilization wire 306 is extended out of the distal end of the main sheath 401 to enable it to be captured by the snare 505 at the distal end of the snare wire 506.

Figure 6:
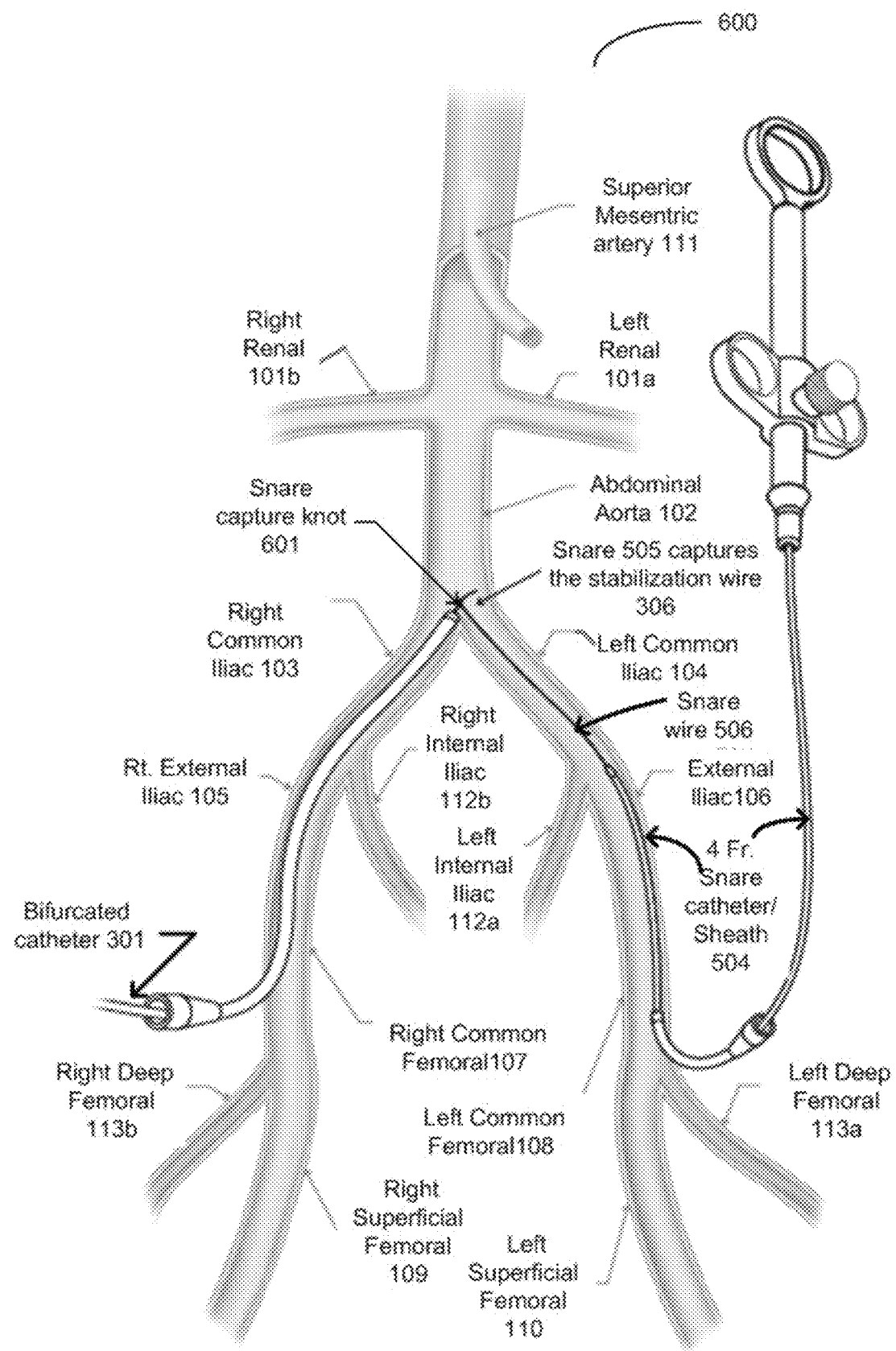
FIG. 6 illustrates the process of inserting the fixed flat stabilization wire bifurcated catheter through the main access sheath from the contralateral access to the aortic bifurcation where the stabilization wire extension is captured by the snare, in accordance with an embodiment of the disclosure.

FIG. 6 illustrates an exemplary process of capturing the stabilization wire 302 by the snare 505 at the end of the snare wire 506, where the stabilization wire 302 extends from the sheath 504 inserted through the access sheath 403 and inserted via the ipsilateral percutaneous access 404. The stabilization wire 306 can be tightened to a snare knot 601. This allows a pull force 703 to be applied to the distal end of the bifurcated catheter 300 from the ipsilateral femoral access 404. The pull force 703 can be applied through the snare catheter 504 and the snare wire 506, which has snared the stabilization wire 306. A push force 701 can also be applied on the proximal end of the bifurcated catheter 300 from the contralateral femoral access 402. The push force 701 and the pull force 703 can be applied simultaneously. The push force 701 and the pull force 703 are used to guide the distal end of the bifurcated catheter 300 with the dilator tip 503 over the aortic bifurcation and down the ipsilateral left iliac arteries 104 and 106.

Figure 7:
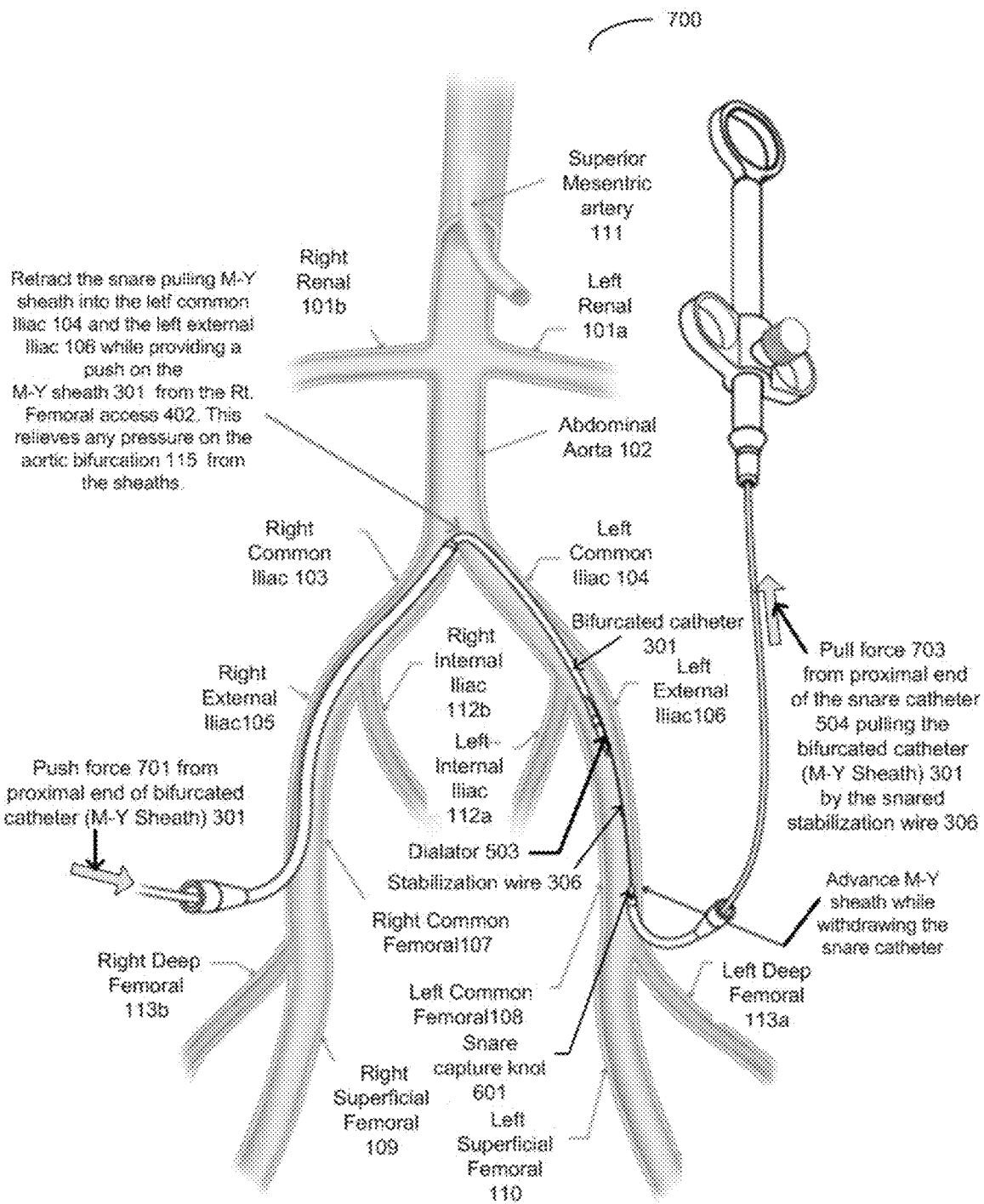
FIG. 7 illustrates the process of pulling the bifurcated catheter down the ipsilateral iliac artery while providing a push force on the proximal end of the bifurcated catheter from the contralateral access, in accordance with an embodiment of the disclosure.

FIG. 7 illustrates a process for advancing the bifurcated catheter 300 into the ipsilateral iliac artery, in accordance with one embodiment of the disclosure. Once guided over the aortic bifurcation and down the ipsilateral left iliac arteries 104 and 106, the bifurcated catheter 300 can be guided to the left common femoral artery 108. The snare wire 506, encompassing the snared stabilization wire 306, can be pulled out of the ipsilateral snare access sheath 403 and anchored outside ipsilateral access 404, and outside the body of the patient.

Figure 8:
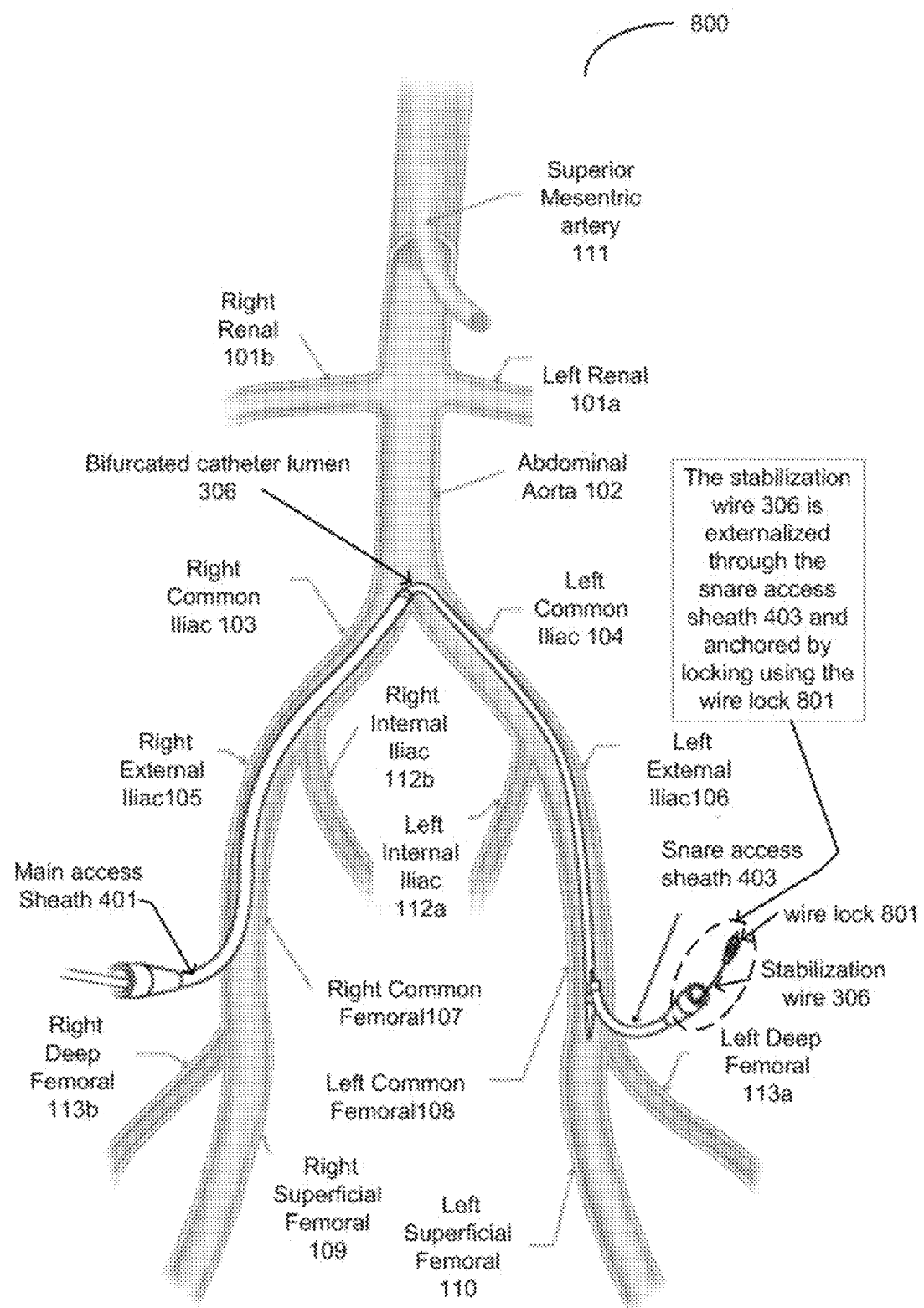
FIG. 8 illustrates the process of pulling the bifurcated catheter into the ipsilateral femoral artery with the stabilization wire externalized and anchored to provide end to end stabilization for the procedural lumen, in accordance with an embodiment of the disclosure.

FIG. 8 illustrates an exemplary process for advancing the bifurcated catheter into the ipsilateral femoral artery while externalizing the stabilization wire 306 and subsequently anchoring it, using a wire lock 801. The bifurcated catheter 300 can be pulled by the snare wire 506, using the snared stabilization wire 306, from the ipsilateral access 404. Simultaneously, the bifurcated catheter can be pushed from the contralateral femoral access 402 to guide the bifurcated sheath down the left common femoral artery 108. The side hole 305 with the stabilization wire 306 of the bifurcated catheter 300 can be positioned at the ipsilateral access 404 by applying the push force 701 to the proximal end of the bifurcated catheter and the pull force to the distal end of the bifurcated catheter 300. The pull force can be applied through the snared stabilization wire 306, snared by the snare wire 506 from the ipsilateral femoral access 404. This push-pull capability can also be used to guide the bifurcated sheath 301 and any procedural catheters within the main procedural lumen 303 of the bifurcated catheter 300 down the narrow and tortuous branches of the femoral artery. For example, the bifurcated sheath 301 can be guided through the superficial femoral artery 110, where the procedure is performed. The snare wire 306 can be externalized and locked external to the snare access sheath 403. At this point it is possible to lock the bifurcated catheter 300 at its proximal end outside the main access sheath 401. The stabilization wire 306 can also be locked at or outside the snare access sheath 403 using a wire lock 801. By locking the stabilization wire 306 outside the snare access sheath 403, locking the bifurcated sheath with the fixed flat wire outside the main access sheath 401 and providing a pull force on the distal end of the bifurcated catheter, a tension can be applied via the bifurcated catheter 300 to any procedural catheter or instruments introduced through the main procedural lumen 303 of the bifurcated catheter 300. This tension can provide stabilization to the main procedural lumen 303 of the bifurcated catheter 300. Any procedural catheters and instruments within the main procedural lumen 303 can also be stabilized using this system and method. Anchoring and locking the stabilization wire can cause bifurcation of the bifurcated catheter at the snare access sheath. This bifurcation can provide an anchor point for procedural catheters and instruments introduced via the procedural lumen 303 of the bifurcated catheter improved pushability and improved accessibility to the procedural sites.

By externalizing the stabilization wire outside the ipsilateral femoral access and fixing the flat wire to the bifurcated catheter 300 outside the contralateral femoral access allow a push/pull force to be applied on the bifurcated catheter 300 and any procedural catheters or instruments inserted through the bifurcated catheter. This push/pull force provides a see-saw motion of the bifurcated catheter 300. This motion can make enable safe and efficient access into tortuous lower extremities of the vasculature, particularly access below the knees of a patient.

Figure 9:
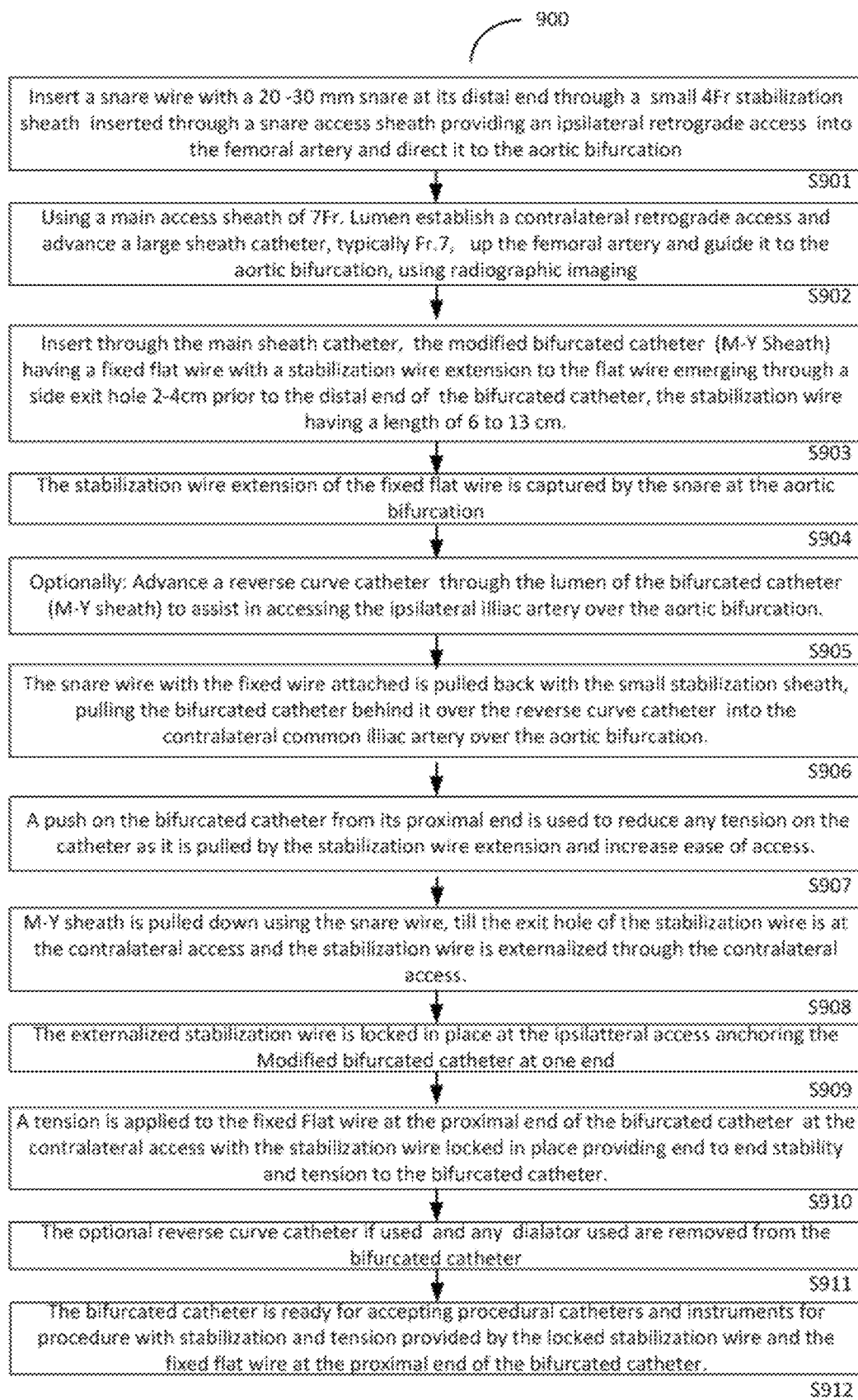
FIG. 9 illustrates a process for providing stability, tension and pushability of the bifurcated catheter, in accordance with an embodiment of the disclosure.

FIG. 9 illustrates an exemplary process 900 for providing stability, tension and pushability of the bifurcated catheter of FIG. 3, for procedures within the left superficial femoral artery.

At step 901, a small lumen snare access sheath is inserted into the left common femoral artery to provide an ipsilateral retrograde access. A snare catheter is inserted through the snare access sheath with a snare wire. The snare catheter can be 4 Fr or smaller. The snare wire can have a 20-30 mm snare at its distal end. In some embodiments, the snare wire can have a snare less than 20 mm at its distal end. The snare wire can be guided to the aortic bifurcation.

At step 902, a main access sheath is used to establish a contralateral retrograde access at the right common femoral artery location. The main access sheath can be a 7 Fr. lumen or larger. A large sheath catheter is advanced up the right femoral artery and the iliac arteries towards the aortic bifurcation. The large sheath catheter can be guided using radiographic imaging. The large sheath catheter can be 7 Fr.

At step 903, a modified bifurcated catheter can be inserted into the main sheath and guided to the aortic bifurcation. The modified bifurcated catheter has a fixed flat wire secured within the main lumen of the bifurcated catheter, from its proximal end to the bifurcation. An extension of the flat wire emerges through a side exit hole at the bifurcation. The extension is the stabilization wire. The side exit hole at the bifurcation can be between 2-4 cm prior to the distal end of the bifurcated catheter. In some embodiments, the stabilization wire can have a length of 6 to 13 cm beyond the side exit hole. In alternative embodiments, the stabilization wire can be extended beyond 13 cm from the side exit hole.

At step 904 the stabilization wire, extending from the side exit hole, is captured by the snare at the distal end of the snare wire. The snare typically captures the stabilization wire at the aortic bifurcation. The snare is tightened to secure the stabilization wire and apply a pull pressure on it.

At step 905 a reverse curve catheter can be inserted through the main lumen of the bifurcated catheter to access the left common iliac artery. The reverse curve catheter can assist in transitioning the bifurcated catheter from the contralateral right common iliac artery to the ipsilateral left common iliac artery over the aortic bifurcation.

At step 906, an external pull force can be applied on the snare wire with the stabilization wire snared, while a push force is applied to the proximal end of the bifurcated catheter 300. The procedural lumen 300 and the bifurcated catheter 300 are able to be pulled and pushed over the reverse curve catheter into the contralateral common left iliac artery.

At step 907 a push force is applied on the bifurcated catheter at its proximal end to assist advance the bifurcated catheter past sharp corners and reduce tension on the catheter as it is pulled by the stabilization wire. The combination of the push and pull force enable the bifurcated catheter to easily overcome obstructions as it traverses down the tortuous curves of the left femoral vessels. The combination of push and pull forces also help to reduce the tension on the bifurcated catheter and increase access while reducing the trauma to the vessels.

At step 908 the bifurcated sheath is simultaneously pulled and pushed down the ipsilateral left side vasculature, until the side exit hole of the stabilization wire is at the ipsilateral snare access sheath location. The stabilization wire is externalized by pulling the snare wire out of the access sheath through the ipsilateral access.

At step 909 the externalized stabilization wire is anchored by locking it in place at the ipsilateral access by a wire lock. The modified bifurcated catheter is anchored at the distal end of the bifurcation.

At step 910, a tension is applied to the fixed Flat wire at the proximal end of the bifurcated catheter. The tension is applied at the contralateral access with the stabilization wire. The stabilization wire can be locked in place at the distal end. An end-to-end application of tension can be applied to provide stability to the bifurcated catheter. This stability increases pushability of any procedural catheters within its main procedural lumen.

At step 911 any optional reverse curve catheter can be removed. Furthermore, any dilator used to reduce trauma to vessels can also be removed from the bifurcated catheter.

At step 912 the bifurcated catheter is configured to accept the procedural catheters and instruments for procedure, through its main lumen. Stabilization and tension can be provided by the locked stabilization wire at the distal end of the bifurcation and the fixed flat wire. The bifurcated catheter is configured for interventional procedures (stents, atherectomy, etc.) within the left peripheral vasculature. The process 900 is terminated after step 912.

The examples provided herein are directed towards specific examples. One of ordinary skill in the art would understand the provided examples are not intended to be exhaustive. There exists other exemplary access and stabilization of a procedural catheter or sheath. As is well understood, the preferred method will vary based on the location of the procedure and the physical condition of the patient.

As is well understood by those familiar with the art, the disclosure may be embodied in other specific forms without departing from the spirit or essential characteristics thereof. Likewise, the naming and division of the members, features, attributes, and other aspects are not mandatory or significant, and the mechanisms that implement the disclosure or its features may have different structural construct, names, and divisions. Accordingly, the disclosure of the disclosure is intended to be illustrative, but not limiting, of the scope of the disclosure.

The embodiments disclosed herein can be implemented as hardware, firmware, software, or any combination thereof.

Moreover, the software is preferably implemented as an application program tangibly embodied on a program storage unit or computer readable medium. The application program may be uploaded to, and executed by, a machine comprising any suitable architecture.

The invention claimed is:

1. A system for performing a lower extremity intervention procedure, the system comprising:
    a bifurcated catheter configured to be inserted through a first percutaneous access in a lower extremity vasculature, the bifurcated catheter comprising a proximal end and a distal end, wherein the distal end of the bifurcated catheter comprises a bifurcation, and wherein the bifurcated catheter further comprises at least one lumen that extends from the proximal end to the distal end of the bifurcated catheter, and wherein the bifurcated catheter further comprises a side hole; and
    a flat wire attached within the at least one lumen of the bifurcated catheter, wherein the flat wire is attached to an inner wall of the at least one lumen of the bifurcated catheter from the proximal end to the bifurcation at the distal end;
    wherein the flat wire is configured to emerge from the side hole and exit a second percutaneous access in a lower extremity vasculature and configured to function as a stabilization wire by the application of an end to end tension to the flat wire.

2. The system of claim 1, wherein the bifurcation is at least 2 cm from the distal end of the bifurcated catheter.

3. The system of claim 1, wherein the flat wire is configured to extend for a length up to 10 cm beyond the bifurcation.

4. The system of claim 1, wherein the bifurcated catheter further comprises a procedural lumen and a stabilization lumen, wherein the stabilization lumen is smaller than the procedural lumen.

5. The system of claim 4, wherein the side hole is in the stabilization lumen.

6. The system of claim 4, wherein the side hole is in the procedural lumen.

7. The system of claim 4, wherein the flat wire is configured to apply tension and stabilization to the procedural lumen for access to a location of the lower extremity intervention procedure.

8. The system of claim 1, further comprising an access sheath configured to provide a percutaneous ipsilateral femoral artery access for a distal end of the flat wire to exit a patient.

9. The system of claim 8, wherein the second percutaneous access is an ipsilateral percutaneous femoral artery access and wherein the first percutaneous access is a contralateral percutaneous femoral artery access,
    wherein a proximal end of the bifurcated catheter is configured to receive a push force to advance the bifurcated catheter through a tortuous peripheral vasculature to the location of the lower extremity intervention procedure.

10. The system of claim 1, wherein the bifurcated catheter is configured to receive a pull force to its distal end from the flat wire and a push force from its proximal end at a contralateral access to advance the bifurcated catheter through tortuous vessels to a site of the lower extremity intervention procedure.

11. A method for performing a lower extremity intervention procedure in a femoral artery of a patient, the method comprising:
    establishing a first percutaneous ipsilateral femoral artery access for a snare access sheath into an ipsilateral femoral artery of a patient to enable an ipsilateral retrograde access for a snare catheter;
    inserting the snare catheter through the snare access sheath, the snare catheter comprising a snare wire having a proximal end and a distal end, the distal end of the snare wire comprising a snare, wherein the proximal end of the snare wire extends out of the percutaneous ipsilateral femoral artery access, and wherein the snare at the distal end of the snare wire is guided to an aortic bifurcation, using radiographic imaging;
    establishing a percutaneous contralateral femoral artery access for a main access sheath into a contralateral femoral artery to enable a contralateral retrograde access;
    advancing the main access sheath through the contralateral retrograde femoral access into the contralateral femoral artery and guiding the main access sheath to the aortic bifurcation, using the radiographic imaging;
    inserting a bifurcated catheter into the main access sheath and guiding a distal end of the bifurcated catheter to the aortic bifurcation; wherein the bifurcated catheter comprises a proximal end and a distal end, wherein the distal end comprises a bifurcation and a side hole at the bifurcation, wherein the bifurcated catheter further comprises a flat wire attached to a lumen of the bifurcated catheter, wherein the flat wire is affixed to the lumen of the bifurcated catheter from the proximal end to the bifurcation at the distal end, wherein the flat wire exits the side hole of the bifurcated catheter;
    capturing a distal end of the flat wire by the snare at the distal end of the snare wire;
    applying a pull force on the proximal end of the snare catheter and the snare wire external to the percutaneous ipsilateral femoral artery access, which applies a pull force on the bifurcated catheter via the flat wire;
    applying a push force, while applying the pull force, to the proximal end of the bifurcated catheter external to the contralateral femoral access, thereby moving the bifurcated catheter over the aortic bifurcation;
    further applying the pull force and the push force simultaneously on the bifurcated catheter to enable the bifurcated catheter to move to the ipsilateral femoral artery over sharp corners, bends and partial blockages while reducing tension on the bifurcated catheter;
    simultaneously pulling and pushing the bifurcated catheter until the side hole of the bifurcated catheter is at the ipsilateral snare access sheath;
    pulling the snare catheter and the snare wire such that the flat wire extends out of the percutaneous ipsilateral femoral artery access through the snare access sheath;
    anchoring the flat wire by locking the flat wire in place external to the ipsilateral snare access sheath using a wire lock, thereby anchoring the bifurcated catheter at the snare access sheath; and
    applying tension to the fixed wire at the proximal end of the bifurcated catheter, at the percutaneous contralateral femoral artery access, wherein the applied tension allows an end-to-end application of tension and stability to the bifurcated catheter, wherein the stability of the bifurcated catheter increases a stability and a pushability of a procedural catheters or instruments within the procedural lumen of the bifurcated catheter for access to a location of a lower extremity intervention procedure.

12. The method of claim 11, further comprising using a dilator during the access of the procedural catheter to the location and removing the dilator prior to the lower extremity intervention procedure.

13. The method of claim 11, wherein the bifurcated catheter is configured to accept procedural catheters and instruments for procedure, through its procedural lumen, with stabilization and tension.

14. The method of claim 11, wherein the bifurcated catheter is configured for interventional procedures within an ipsilateral vasculature.

15. The method of claim 11, wherein flat wire enables a sea-saw movement of the bifurcated catheter, enabling access to a location of the procedure below the bifurcation of the bifurcated catheter through tortuous vasculature.

16. The method of claim 11, wherein using a combination of push and pull forces that are applied on the bifurcated catheter via the flat wire reduce tension on the bifurcated catheter and increased ease of access while reducing the trauma to vessels within the femoral artery of a patient during access to the location of the lower extremity intervention procedure.

* * * * *